United States Patent
Qashou et al.

(10) Patent No.: US 6,926,931 B2
(45) Date of Patent: Aug. 9, 2005

(54) DUAL SIDED NONWOVEN CLEANING ARTICLES

(75) Inventors: Imad Qashou, Cornelius, NC (US); Rick Augustine, Sherrills Ford, NC (US); Karl Kelly, Holly Springs, NC (US); Mark Landreth, Mooresville, NC (US); Patrick Barge, Cornelius, NC (US); Mike Disotelle, Mooresville, NC (US); Nick Carter, Mooresville, NC (US)

(73) Assignee: Polymer Group, Inc., North Charleston, SC (US)

( * ) Notice: Subject to any disclaimer, the term of this patent is extended or adjusted under 35 U.S.C. 154(b) by 0 days.

(21) Appl. No.: 10/818,271

(22) Filed: Apr. 5, 2004

(65) Prior Publication Data

US 2004/0265498 A1 Dec. 30, 2004

Related U.S. Application Data

(60) Provisional application No. 60/460,905, filed on Apr. 7, 2003.

(51) Int. Cl.⁷ .............................................. B05D 1/00
(52) U.S. Cl. ................................................. 427/394
(58) Field of Search ................................ 427/394, 396

(56) References Cited

U.S. PATENT DOCUMENTS

| | | |
|---|---|---|
| 3,929,678 A | 12/1975 | Laughlin et al. |
| 4,041,203 A | 8/1977 | Brock et al. |
| 4,100,324 A * | 7/1978 | Anderson et al. ............ 442/344 |
| 4,741,941 A * | 5/1988 | Englebert et al. ............. 428/71 |
| 4,853,281 A * | 8/1989 | Win et al. .................... 442/118 |
| 5,043,155 A | 8/1991 | Puchalski et al. |
| 5,098,764 A | 3/1992 | Bassett et al. |
| 5,108,642 A | 4/1992 | Aszman et al. |
| 5,169,706 A * | 12/1992 | Collier et al. ................ 428/152 |
| 5,284,703 A * | 2/1994 | Everhart et al. ............. 442/401 |
| 5,302,446 A * | 4/1994 | Horn .......................... 442/333 |
| 5,350,624 A * | 9/1994 | Georger et al. .............. 428/219 |
| 5,534,265 A | 7/1996 | Fowler et al. |
| 5,643,653 A * | 7/1997 | Griesbach et al. ........... 428/120 |
| 5,648,083 A | 7/1997 | Blieszner et al. |
| 6,028,018 A * | 2/2000 | Amundson et al. .......... 442/381 |
| 6,103,683 A * | 8/2000 | Romano et al. ............. 510/383 |
| 6,340,663 B1 | 1/2002 | Deleo et al. |
| 6,534,472 B1 | 3/2003 | Arvanitidou et al. |
| 2003/0200991 A1 * | 10/2003 | Keck et al. ..................... 134/6 |
| 2004/0105965 A1 * | 6/2004 | Qashou et al. ............... 428/196 |
| 2004/0110443 A1 * | 6/2004 | Pelham ........................ 442/400 |
| 2004/0128807 A1 * | 7/2004 | Qashou et al. ................. 28/107 |

FOREIGN PATENT DOCUMENTS

| | | | |
|---|---|---|---|
| WO | WO 01 / 00917 | * | 1/2001 |
| WO | WO 01 / 47705 | * | 5/2001 |
| WO | WO 03 / 093557 | * | 11/2003 |
| WO | WO 03 / 095731 | * | 11/2003 |
| WO | WO 2004 / 053219 | * | 6/2004 |

* cited by examiner

Primary Examiner—Erma Cameron
(74) Attorney, Agent, or Firm—Wood, Phillips, Katz, Clark & Mortimer

(57) ABSTRACT

The present invention relates to a dual performance cleaning article, wherein said cleaning article is comprised of a first abrasive meltblown surface that facilitates the process of loosening particulates, such as dust and dirt, and an opposing second soft, air permeable surface, which is capable of absorbing and/or picking up particulates and liquids. The meltblown layer comprises coarse discontinuous filamentary elements, formed from adjusting the variable commonly utilized in the traditional meltblown method.

12 Claims, 5 Drawing Sheets

DUAL SIDED NONWOVEN CLEANING ARTICLES

TECHNICAL FIELD

The present invention relates generally to a cleaning article, and specifically to a dual performance cleaning article comprising two functionally diverse surfaces, wherein said article has an abrasive side that facilitates the process of loosening particulates, such as dust and dirt, and an opposing soft, absorbent side, such material being imminently suitable for application in cleaning and cleansing applications.

BACKGROUND OF THE INVENTION

The general use of nonwoven fabrics as cleaning and cleansing articles is well known in the art. Various end-use articles are commercially available which utilize a combination of topical, performance enhancing additives and/or multi-layered laminate constructions. Enhanced versions of articles used in cleaning hard-surfaces further incorporate an optional cleaning fluid, including but not limited to, disinfectants, polishing solutions, and glass cleaners.

One such layer commonly utilized in a multi-layer cleaning construct is a meltblown layer. Meltblown layers are often incorporated into cleaning articles in order to provide the article with absorbent and/or abrasive features. A meltblown layer is comprised of micrometer scale filaments, which are drawn and fragmented by a high velocity air stream, and deposited into a self-annealing mass. The meltblowing process is well known in the art and described in U.S. Pat. No. 4,041,203, to Brock, et al., which is hereby incorporated by reference. Combining a meltblown layer along with various other nonwoven layers, allows for an end-use article that can perform multiple tasks.

It has become desirable, by way of convenience, to be able to utilize a single cleaning article for multiple tasks, wherein a single use wipe can abrade and/or disrupt a build up of dust or dirt, as well as, absorb or collect any resultant particulates and liquids. The present invention contemplates a dual performance cleaning article, wherein one surface is comprised of an abrasive meltblown layer and the opposing surface is comprised of a soft, absorbent, nonwoven layer. Further, the wipe of the invention is drapeable exhibiting the ability to conform to the surface being cleaned. Further still, the invention efficiently integrates two separate cleaning articles into a single disposable cleaning article, thus promoting efficient manufacture, while obtaining the desired dual task management.

SUMMARY OF THE INVENTION

The present invention relates to a dual performance cleaning article, wherein said cleaning article is comprised of a first abrasive meltblown surface that facilitates the process of loosening particulates, such as dust and dirt, and an opposing second soft, air permeable surface, which is capable of absorbing and/or picking up particulates and liquids. The meltblown layer comprises coarse discontinuous filamentary elements, formed from adjusting the variable commonly utilized in the traditional meltblown method. Such filamentary elements may be formed from a polymer selected from the group consisting of polyolefins, polyesters, polyetheresters, and polyamide. Suitable absorbent, air permeable webs include, but are not limited to filamentary webs and fibrous carded webs comprised of natural fiber, synthetic fibers, and the blends thereof.

In accordance with the present invention, the nonwoven cleaning article is comprised of a meltblown layer and a soft, absorbent layer that are integrated by hydroentanglement on an image transfer device. It is contemplated that nonwovens embodying the principles of the present invention are especially suitable as a wet wipe substrate for cleaning both domestic and industrial surfaces, and further for use in skin/facial cleaning. The present nonwoven fabric wipe can be provided in forms that are suitable for use as a dry wipe to absorb liquid, and to provide extra scrubbing effect, as needed.

It is within the purview of the present invention to optionally utilize specific additives or a combination of additives, so as to enhance the performance, visual appearance, or aromatic properties, wherein such additives are meant to include, but not limited to anti-microbial or disinfecting agents, pigments, and/or fragrances. Such enhancing agents may be provided in the form of a melt-additive in the polymer from which the coarse meltblown layer is formed, or may comprise a post surface treatment applied to the laminate itself or deposited into a container or film packaging from which the end-use article may be dispensed.

Other features and advantages of the present invention will become readily apparent from the following detailed description, the accompanying drawings, and the appended claims.

DETAILED DESCRIPTION

Figure 1:
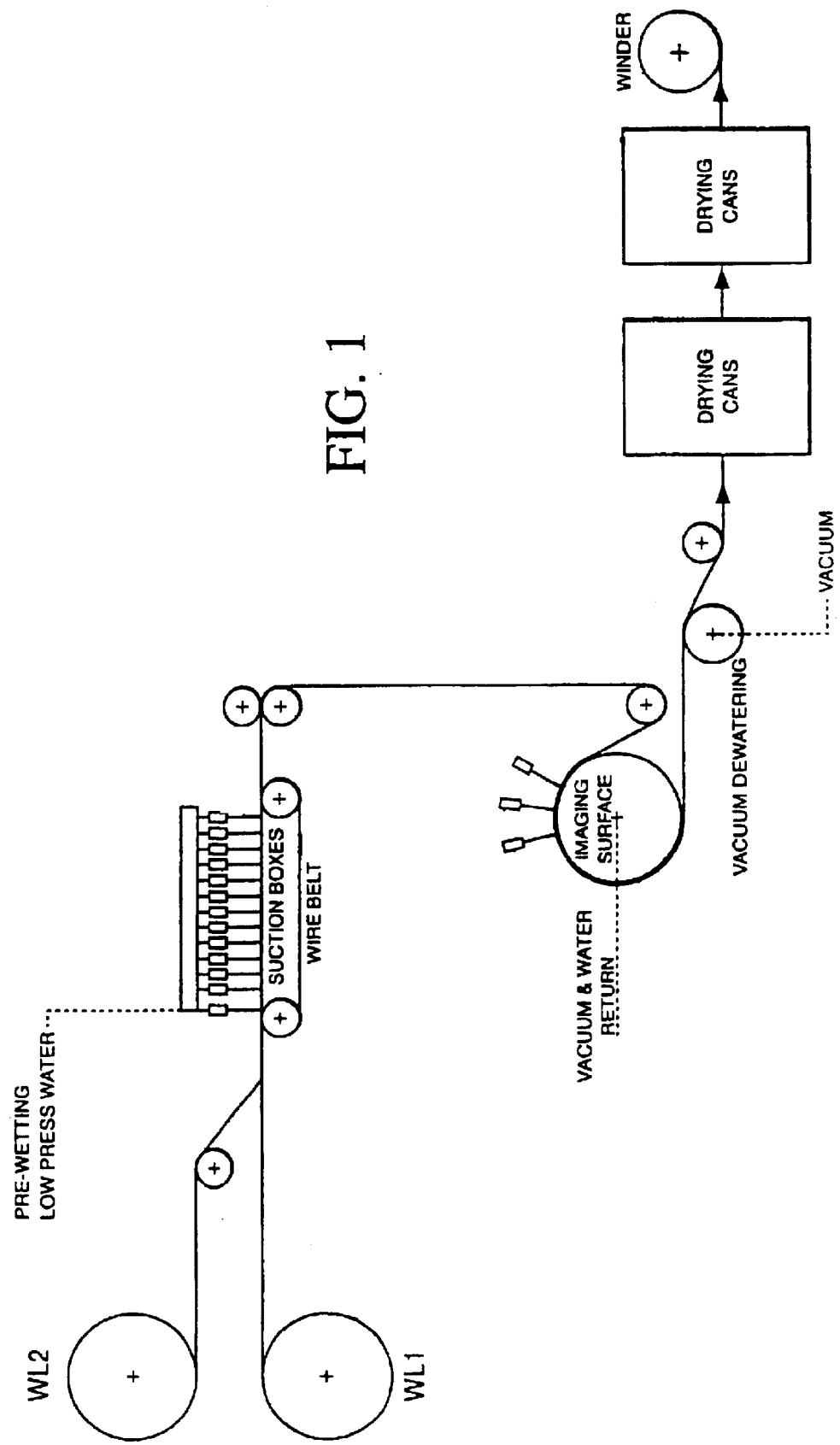
FIG. 1 is a diagrammatic view of a forming apparatus for forming a nonwoven cleaning article in accordance with the principles of the present invention.
Figure 2:
FIG. 2 is a photomicrograph of the abrasive side of the nonwoven cleaning article in practicing the present invention.
Figure 3:
FIG. 3 is a photomicrograph of the soft, absorbent side of the nonwoven cleaning article in practicing the present invention.
Figure 4:
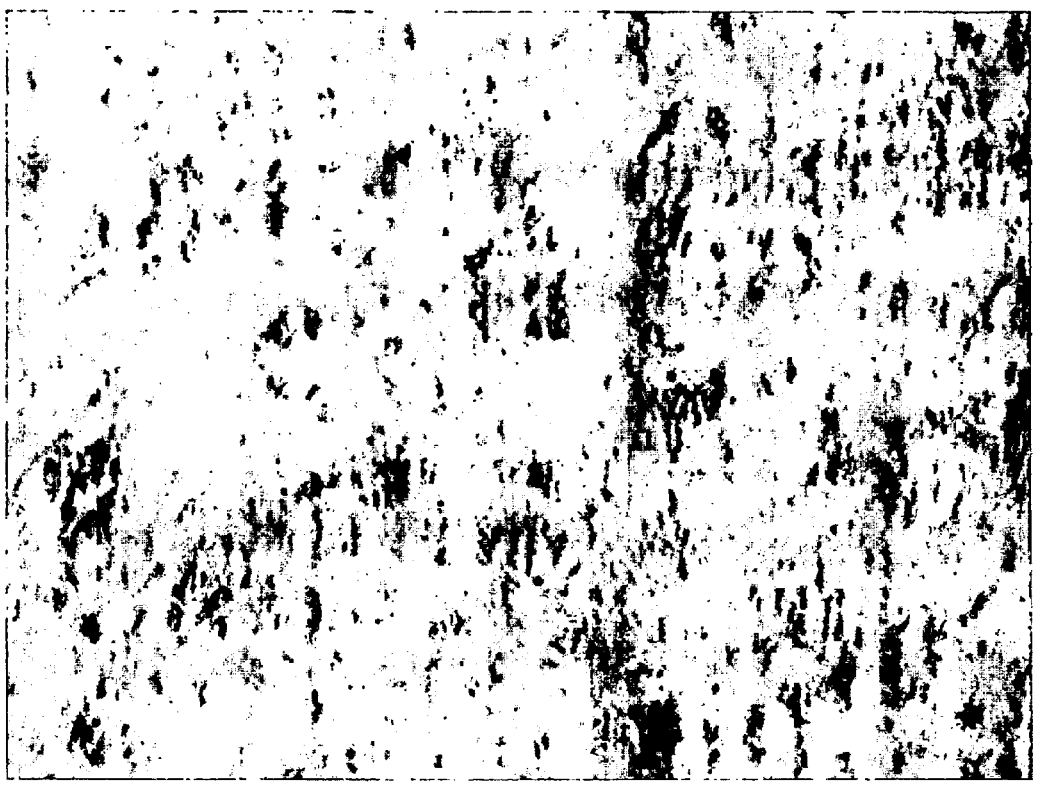
FIG. 4 is a photomicrograph on a macroscopic scale of the abrasive side of the nonwoven cleaning article in practicing the present invention.
Figure 5:
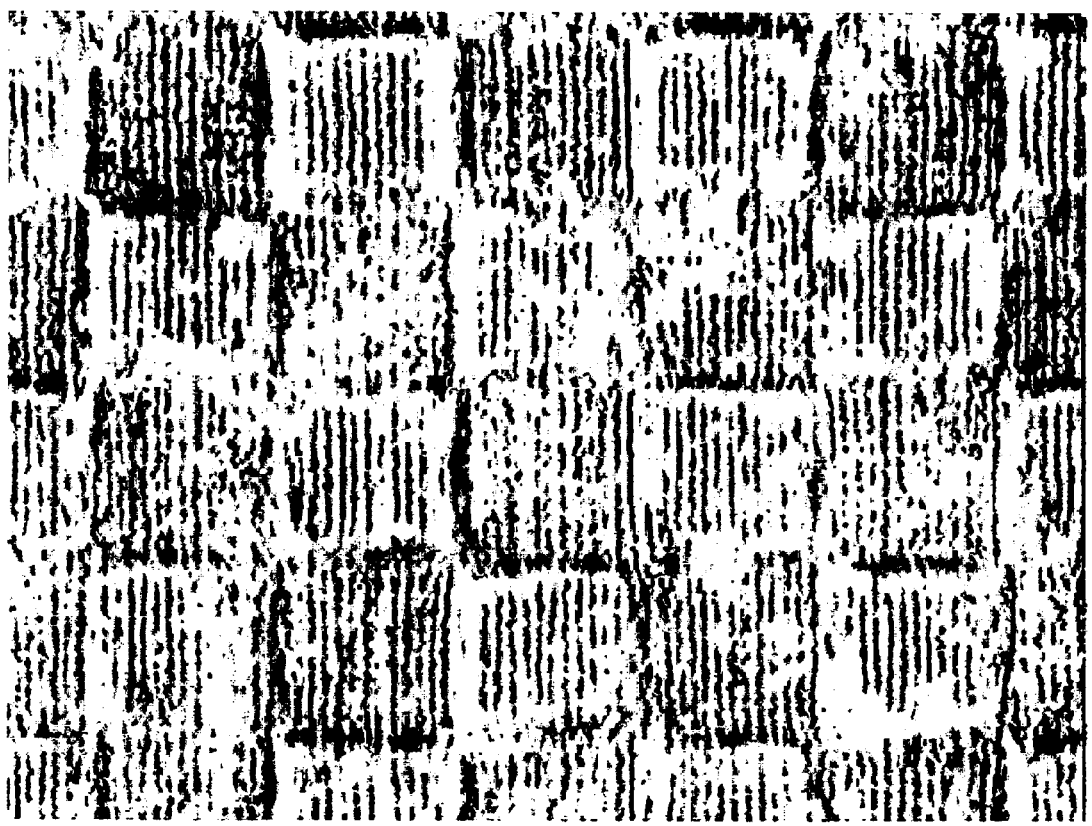
FIG. 5 is a photomicrograph on a macroscopic scale of the soft, absorbent side of the nonwoven cleaning article in practicing the present invention.

While the present invention is susceptible of embodiment in various forms, there will hereinafter be described, presently preferred embodiments, with the understanding that the present disclosure is to be considered as an exemplification of the invention, and is not intended to limit the invention to the specific embodiments disclosed herein.

The nonwoven cleaning article of the present invention is comprised of coarse denier meltblown filaments, wherein a spunbond resin is utilized with a conventional meltblown process so as to capture thicker filaments. In general, the meltblown process utilizes a molten polymer is extruded under pressure through orifices in a spinneret or die. Traditionally, high velocity air impinges upon and entrains the filaments as they exit the die. Usually the energy of this step is such that the formed filaments are greatly reduced in diameter and are fractured so that microfibers of finite length are produced. Utilizing a spunbond resin with a lower melt flow rate, as well as lowering the air pressure, however, allows the collected filaments to take on a thicker diameter, providing the overall collective web with a desirable coarse texture. The process to form either a single layer or a multiple-layer fabric is continuous, that is, the process steps are uninterrupted from extrusion of the filaments to form the first layer until the bonded web is wound into a roll. Methods for producing these types of fabrics are described in U.S. Pat. No. 4,041,203, hereby incorporated by reference. The resultant filaments may be of various cross-sectional profiles, which are not considered a limitation to the practice of the present invention.

In a particular embodiment, a polypropylene spunbond resin, commercially known as PP3155 made available by Exxon Chemical Company was utilized. The aforementioned resin had a 35 MFR and was extruded at an average die temperature of 562° Fahrenheit with an approximate throughput of 7.1 grams/hole/min. Further, the distance between the meltblown die and the collective surface was around the order of 19 inches. The resultant meltblown filaments have a denier between that of 5 and 50 microns. Suitable polymers that may be used in the meltblowing process of the present invention include those selected from the group consisting of polyolefins, polyesters, polyetheresters, and polyamide.

Optionally, prior to extrusion, the single polymeric resin can be compounded with various melt-additives, so as to assist with the processing conditions, enhance the performance of the web, or enhance the appearance of the web, such additives including, but not limited to thermal stabilizers, colorants, and aromatics.

The dual purpose cleaning wipe of the present invention also comprises a soft, absorbent layer capable of picking up liquids and particulates. A nonwoven of this nature may be a fibrous nonwoven layer or a continuous filament nonwoven layer. In general, continuous filament nonwoven fabric formation involves the practice of the spunbond process. A spunbond process involves supplying a molten polymer, which is then extruded under pressure through a large number of orifices in a plate known as a spinneret or die. The resulting continuous filaments are quenched and drawn by any of a number of methods, such as slot draw systems, attenuator guns, or Godet rolls. The continuous filaments are collected as a loose web upon a moving foraminous surface, such as a wire mesh conveyor belt. When more than one spinneret is used in line for the purpose of forming a multi-layered fabric, the subsequent webs are collected upon the uppermost surface of the previously formed web. The web is then at least temporarily consolidated, usually by means involving heat and pressure, such as by thermal point bonding. Using this means, the web or layers of webs are passed between two hot metal rolls, one of which has an embossed pattern to impart and achieve the desired degree of point bonding, usually on the order of 10 to 40 percent of the overall surface area being so bonded.

When staple fibers are utilized to form the absorbent nonwoven layer, the fibers may begin in a bundled form as a bale of compressed fibers. In order to decompress the fibers, and render the fibers suitable for integration into a nonwoven fabric, the bale is bulk-fed into a number of fiber openers, such as a garnet, then into a card. The card further frees the fibers by the use of co-rotational and counter-rotational wire combs, then depositing the fibers into a lofty batt. The lofty batt of staple fibers can then optionally be subjected to fiber reorientation, such as by air-randomization and/or cross-lapping, depending upon the ultimate tensile properties of the resulting nonwoven fabric. The fibrous batt is integrated into a nonwoven fabric by application of suitable bonding means, including, but not limited to, use of adhesive binders, thermobonding by calender or through-air oven, and hydroentanglement.

In one embodiment, the absorbent precursor web and the meltblown precursor web are juxtaposed and hydroentangled on a three-dimensional image transfer device. Such three-dimensional image transfer devices are disclosed in U.S. Pat. No. 5,098,764, which is hereby incorporated by reference. The two precursor webs may be advanced onto the three-dimensional image transfer device so that the meltblown precursor web is facing the hydraulic jets of the hydroentanglement process and the absorbent precursor web is in contact with the three-dimensional transfer device. Hydroentangling the precursor webs in this manner allows for the meltblown filaments to become more integrated into the absorbent precursor web. FIG. 1 is representative of the hydroentangling apparatus utilized in the formation of the fabric of the present invention. Further, the meltblown filaments fragment with the force of the water through the meltblown web. The resultant laminate is more drapeable due to the hydraulic pressure affecting the meltblown filaments by fragmenting the filaments.

In a second embodiment, the absorbent precursor web and the meltblown precursor web are juxtaposed and hydroentangled on a three-dimensional image transfer device. The two precursor webs may be advanced onto the three-dimensional image transfer device so that the absorbent precursor web is facing the hydraulic jets of the hydroentanglement process and the meltblown web is in contact with the three-dimensional transfer device. Hydroentangling the precursor webs in this manner allows for the meltblown filaments to remain substantially more in tact. The resultant article is stiffer due to minimal fragmentation of the meltblown filaments.

In a third embodiment, the meltblown filaments are extruded and collected directly onto the absorbent precursor web and then subsequently hydroentangled on a three-dimensional image transfer device.

Optionally, the dual performance nonwoven cleaning article may comprise an additional layer, including, but not limited to a microporous film, a supportive member, such as a spunbond or mesh scrim, or a barrier layer of sorts. Further, the article may be comprised of apertures of varying shapes and sizes wherein the apertures extend either partially or entirely though the laminate. Further still, the article may optionally be impregnated with a cleaning agent or placed within a tub or other packaging means containing the desired cleaning agent.

The dual performance cleaning article embodying the principles of the present invention are suitable as a dry or wet wipe substrate for cleaning both domestic and industrial surfaces, and further for use in skin/facial cleaning. The present nonwoven fabric wipe can be provided in forms that are suitable for use as a dry wipe to absorb liquid, and to provide extra scrubbing effect, as needed. FIGS. 2–5 are photomicrographs depicting the fabric of the present invention.

In accordance with the present invention, the dual sided nonwoven article includes the use of various aqueous and non-aqueous compositions. The dual performance article embodying the principles of the present invention is especially suitable for home care cleaning or cleansing articles. The dual sided nonwoven article may be used in various home care applications, wherein the end use article may be a dry or wet hand held sheet, such as a wipe, a mitt formation, or a cleaning implement capable of retaining the dual sided article. The various end uses suitable for cleaning household surfaces such as, kitchen and bathroom countertops, sinks, bathtubs, showers, appliances, and fixtures.

Cleaning compositions suitable for such end use applications include those that are described in U.S. Pat. No. 6,103,683 to Romano, et al., U.S. Pat. No. 6,340,663 to Deleo, et al., U.S. Pat. No. 5,108,642 to Aszman, et al., and U.S. Pat. No. 6,534,472 Arvanitidou, et al., all of which are hereby incorporated by reference. Selected cleaning compositions may also include surfactants, such as alkylpolysaccharides, alkyl ethoxylates, alkyl sulfonates, and mixtures thereof; organic solvent, mono- or polycarboxylic acids, odor control agents, such as cyclodextrin, peroxides, such as benzoyl peroxide, hydrogen peroxide, and mixtures thereof, thickening polymers, aqueous solvent systems, suds suppressors, perfumes or fragrances, and detergent adjuvants, such as detergency builder, buffer, preservative, antibacterial agent, colorant, bleaching agents, chelants, enzymes, hydrotropes, and mixtures thereof. The aforementioned compositions preferably comprise from about 50% to about 500%, preferably from about 200% to about 400% by weight of the dual sided nonwoven cleaning article.

The dual performance article embodying the principles of the present invention is also suitable for personal cleaning or cleansing articles. Non-limiting examples of such applications include dry or wet facial wipes, body wipes, and baby wipes. Suitable methods for the application of various aqueous and non-aqueous compositions comprise aqueous/alcoholic impregnates, including flood coating, spray coating or metered dosing. Further, more specialized techniques, such as Meyer Rod, floating knife or doctor blade, which are typically used to impregnate cleansing solutions into absorbent sheets, may also be used. The following compositions preferably comprise from about 50% to about 500%, preferably from about 200% to about 400% by weight of the dual sided nonwoven article.

The nonwoven laminate may incorporate an alpha-hydroxycarboxylic acid, which refers not only the acid form but also salts thereof. Typical cationic counterions to form the salt are the alkali metals, alkaline earth metals, ammonium, $C_2$–$C_8$ trialkanolammonium cation and mixtures thereof. The term "alpha-hydroxycarboxylic acids" include not only hydroxyacids but also alpha-ketoacids and related compounds of polymeric forms of hydroxyacid.

Amounts of the alpha-hydroxycarboxylic acids may range from about 0.01 to about 20%, preferably from about 0.1 to about 15%, more preferably from about 1 to about 10%, optimally from about 3 to about 8% by weight of the composition which impregnates the substrate. The amount of impregnating composition relative to the substrate may range from about 20:1 to 1:20, preferably from 10:1 to about 1:10 and optimally from about 2:1 to about 1:2 by weight.

Further, a humectant may be incorporated with the aforementioned alpha-hydroxycarboxylic compositions. Humectants are normally polyols. Representative polyols include glycerin, diglycerin, polyalkylene glycols and more preferably alkylene polyols and their derivatives. Amounts of the polyol may range from about 0.5 to about 95%, preferably from about 1 to about 50%, more preferably from about 1.5 to 20%, optimally from about 3 to about 10% by weight of the impregnating composition.

A variety of cosmetically acceptable carrier vehicles may be employed although the carrier vehicle normally will be water. Amounts of the carrier vehicle may range from about 0.5 to about 99%, preferably from about 1 to about 80%, more preferably from about 50 to about 70%, optimally from about 65 to 75% by weight of the impregnating composition.

Preservatives can desirably be incorporated protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Preservatives are preferably employed in amounts ranging from 0.01% to 2% by weight of the composition.

The cosmetic composition may further include herbal extracts. Illustrative extracts include Roman Chamomile, Green Tea, Scullcap, Nettle Root, Swertia laponica, Fennel and Aloe Vera extracts. Amount of each of the extracts may range from about 0.001 to about 1%, preferably from about 0.01 to about 0.5%, optimally from about 0.05 to about 0.2% by weight of a composition.

Additional cosmetic additives may also include vitamins such as Vitamin E Acetate, Vitamin C, Vitamin A Palmitate, Panthenol and any of the Vitamin B complexes. Anti-irritant agents may also be present including those of steviosides, alpha-bisabolol and glycyhrizzinate salts, each vitamin or anti-irritant agent being present in amounts ranging from about 0.001 to about 1.0%, preferably from about 0.01 to about 0.3% by weight of the composition.

These impregnating compositions of the present invention may involve a range of pH although it is preferred to have a relatively low pH, for instance, a pH from about 2 to about 6.5, preferably from about 2.5 to about 4.5.

In addition to cosmetic compositions, lotions may be incorporated into the dual sided nonwoven article. The lotion preferably also comprises one or more of the following: an effective amount of a preservative, an effective amount of a humectant, an effective amount of an emollient; an effective amount of a fragrance, and an effective amount of a fragrance solubilizer.

As used herein, an emollient is a material that softens, soothes, supples, coats, lubricates, or moisturizes the skin. The term emollient includes, but is not limited to, conventional lipid materials (e.g. fats, waxes), polar lipids (lipids that have been hydrophylically modified to render them more water soluble), silicones, hydrocarbons, and other solvent materials. Emollients useful in the present invention can be petroleum based, fatty acid ester type, alkyl ethoxylate type, fatty acid ester ethoxylates, fatty alcohol type, polysiloxane type, mucopolysaccharides, or mixtures thereof.

Humectants are hygroscopic materials that function to draw water into the stratum corneum to hydrate the skin. The water may come from the dermis or from the atmosphere. Examples of humectants include glycerin, propylene glycol, and phospholipids.

Fragrance components, such as perfumes, include, but are not limited to water insoluble oils, including essential oils. Fragrance solubilizers are components which reduce the tendency of the water insoluble fragrance component to precipitate from the lotion. Examples of fragrance solubilizers include alcohols such as ethanol, isopropanol, benzyl alcohol, and phenoxyethanol; any high HLB (HLB greater than 13) emulsifier, including but not limited to polysorbate; and highly ethoxylated acids and alcohols.

Preservatives prevent the growth of micro-organisms in the liquid lotion and/or the substrate. Generally, such preservatives are hydrophobic or hydrophilic organic molecules. Suitable preservatives include, but are not limited to parabens, such as methyl parabens, propyl parabens, and combinations thereof.

The lotion can also comprise an effective amount of a kerotolytic for providing the function of encouraging healing of the skin. An especially preferred kerotolytic is Allantoin ((2,5-Dioxo-4-Imidazolidinyl)Urea), a heterocyclic organic compound having an empirical formula $C_4H_6N_4O_3$. Allantoin is commercially available from Tri-K Industries of Emerson, N.J. It is generally known that hyperhydrated skin is more susceptible to skin disorders, including heat rash, abrasion, pressure marks and skin barrier loss. A premoistened wipe according to the present invention can include an effective amount of allantoin for encouraging the healing of skin, such as skin which is over hydrated.

U.S. Pat. No. 5,534,265 issued Jul. 9, 1996; U.S. Pat. No. 5,043,155 issued Aug. 27, 1991; and U.S. Pat. No. 5,648,083 issued Jul. 15, 1997 are incorporated herein by reference for the purpose of disclosing additional lotion ingredients.

The lotion can further comprise between about 0.1 and about 3 percent by eight Allantoin, and about 0.1 to about 10 percent by weight of an aloe extract, such as aloe vera, which can serve as an emollient. Aloe vera extract is available in the form of a concentrated powder from the Rita Corporation of Woodstock, Ill.

Further, latherants may be incorporated within the dual sided cleaning article. Non-limiting examples of anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975, all of which are incorporated by reference herein in their entirety. A wide variety of anionic lathering surfactants are useful herein. Non-limiting examples of anionic lathering surfactants include those selected from the group consisting of sarcosinates, sulfates, isethionates, taurates, phosphates, lactylates, glutamates, and mixtures thereof.

Non-limiting examples of nonionic lathering surfactants and amphoteric surfactants for use in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate. Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Additional compositions utilized in accordance with the present invention can comprise a wide range of optional ingredients. The CTFA International Cosmetic ingredient Dictionary, Sixth Edition, 1995, which is incorporated by reference herein in its entirety, describes a wide variety of non-limiting cosmetic and pharmaceutical ingredients commonly used in the skin care industry, which are suitable for use in the compositions of the present invention. Non-limiting examples of functional classes of ingredients are described at page 537 of this reference. Examples of these functional classes include: abrasives, anti-acne agents, anti-caking agents, antioxidants, binders, biological additives, bulking agents, chelating agents, chemical additives, colorants, cosmetic astringents, cosmetic biocides, degreasers, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

The aforementioned classes of ingredients are incorporated in a safe and effective amount. The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgment.

In addition to home care and personal care end uses, the nonwoven cleaning article may be used in industrial and medical applications. For instance, the dual sided laminate may be useful in paint preparation and cleaning outdoor surfaces, such as lawn furniture, grills, and outdoor equipment, wherein the low linting attributes of the laminate may be desirable. Aqueous or non-aqueous functional industrial solvents include, oils, such as plant oils, animal oils, terpenoids, silicon oils, mineral oils, white mineral oils, paraffinic solvents, polybutylenes, polyisobutylenes, polyalphaolefins, and mixtures thereof, toluenes, sequestering agents, corrosion inhibitors, abrasives, petroleum distillates, and the combinations thereof.

A dual side medical cleaning article may incorporate an antimicrobial composition, including, but not limited to iodines, alcohols, such as such as ethanol or propanol, biocides, abrasives, metallic materials, such as metal oxide, metal salt, metal complex, metal alloy or mixtures thereof, bacteriostatic complexes, bactericidal complexs, and the combinations thereof.

The dual sided cleaning article of the present invention is particularly suitable for dispensing from a tub of stacked, folded wipes, or for dispensing as "pop-up" wipes, in which the cleaning article is stored in the tub as a perforated continuous roll, wherein upon pulling a wipe out of the tub, an edge of the next wipe is presented for easy dispensing. The wipes of the present invention can be folded in any of various known folding patterns, such as C-folding, but is preferably Z-folded. A Z-folded configuration enables a folded stack of wipes to be interleaved with overlapping portions. The dual sided cleaning article may be packaged in What us claimed is:

1. A method of making a nonwoven dual sided home care cleaning article comprising the steps of:
   a. providing a three-dimensionally imaged nonwoven fabric comprised of an absorbent precursor web, and a meltblown precursor web comprising filaments in the range of 5–50 microns, wherein said webs are hydroentangled on a three-dimensional image transfer device to form said cleaning article; and
   b. a cleansing composition comprising an effective amount of a cleansing surfactant, said cleansing composition being coated onto and/or impregnated into said fabric to the extent of from 50% to 500% by weight of the fabric.

2. A method of making a nonwoven dual sided home care cleaning article as in claim 1, wherein said cleansing composition is an aqueous or non-aqueous composition.

3. A method of making a nonwoven dual sided home care cleaning article as in claim 1, wherein said cleansing composition includes one or more compositions selected from the group consisting of alkylpolysaccharides, alkyl ethoxylates, alkyl sulfonates, organic solvents, mono- or polycarboxylic acids, odor control agents, peroxides, hydrogen peroxides, thickening polymers, aqueous solvent systems, suds suppressors, perfumes or fragrances, detergent adjuvants, buffers, preservatives, antibacterial agents, colorants, bleaching agents, abrasive compounds, degreasers, chelants, enzymes, hydrotropes, and the combinations thereof.

4. A method of making a nonwoven dual sided personal care cleaning article comprising the steps of:
   a. providing a three-dimensionally imaged nonwoven fabric comprised of an absorbent precursor web, and a meltblown precursor web comprising filaments in the range of 5–50 microns, wherein said webs are hydroentangled on a three-dimensional image transfer device to form said cleaning article; and
   b. a cleansing composition comprising an effective amount of a cleansing surfactant, said cleansing composition being coated onto or impregnated into said fabric to the extent of from 50% to 500% by weight of the fabric.

5. A method of making a nonwoven dual sided personal care cleaning article as in claim 4, wherein said cleansing composition is an aqueous or non-aqueous composition.

6. A method of making a nonwoven dual sided personal care cleaning article as in claim 4, wherein said cleansing composition includes one or more compositions selected from the group consisting of abrasives, anti-acne agents, anticaking agents, antioxidants, binders, biological additives, bulking agents, chelating agents, chemical additives, natural additives, colorants, vitamins, cosmetic astringents, cosmetic biocides, denaturants, drug astringents, emulsifiers, external analgesics, film formers, fragrance components, humectants, emollients, opacifying agents, plasticizers, preservatives, propellants, reducing agents, skin bleaching agents, skin-conditioning agents, skin protectants, solvents, foam boosters, hydrotropes, solubilizing agents, suspending agents, sunscreen agents, ultraviolet light absorbers, viscosity increasing agents, and the combinations thereof.

7. A method of making a nonwoven dual sided industrial cleaning article comprising the steps of:
   a. providing a three-dimensionally imaged nonwoven fabric comprised of an absorbent precursor web, and a meltblown precursor web comprising filaments in the range of 5–50 microns, wherein said webs are hydroentangled on a three-dimensional image transfer device to form said cleaning article; and
   b. a cleansing composition comprising an effective amount of a cleansing surfactant, said cleansing composition being coated onto and/or impregnated into said fabric to the extent of from 50% to 500% by weight of the fabric.

8. A method of making a nonwoven dual sided industrial cleaning article as in claim 7, wherein said cleansing composition is an aqueous or non-aqueous composition.

9. A method of making a nonwoven dual sided industrial cleaning article as in claim 7, wherein said cleansing composition includes one or more compositions selected from the group consisting of oils, paraffinic solvents, polybutylenes, polyisobutylenes, polyalphaolefins, toluenes, sequestering agents, corrosion inhibitors, abrasives, petroleum distillates, and the combinations thereof.

10. A method of making a nonwoven dual sided medical cleaning article comprising the steps of:
    a. providing a three-dimensionally imaged nonwoven fabric comprised of an absorbent precursor web, and a meltblown precursor web comprising filaments in the range of 5–50 microns, wherein said webs are hydroentangled on a three-dimensional image transfer device to form said cleaning article; and
    b. a cleansing composition comprising an effective amount of a cleansing surfactant, said cleansing composition being coated onto and/or impregnated into said fabric to the extent of from 50% to 500% by weight of the fabric.

11. A method of making a nonwoven dual sided personal care cleaning article as in claim 10, wherein said cleansing composition is an aqueous or non-aqueous composition.

12. A method of making a nonwoven dual sided personal care cleaning article as in claim 10, wherein said cleansing composition includes one or more compositions selected from the group consisting of iodines, alcohols, biocides, abrasives, metallic materials, bacteriostatic complexes, bactericidal complexes, and the combinations thereof.

* * * * *